(12) United States Patent
Brown

(10) Patent No.: US 8,172,780 B2
(45) Date of Patent: *May 8, 2012

(54) HIP BRACE APPARATUS AND METHOD OF USE

(76) Inventor: Randall Brown, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/832,863

(22) Filed: Jul. 8, 2010

(65) Prior Publication Data
US 2011/0009790 A1 Jan. 13, 2011

Related U.S. Application Data

(63) Continuation of application No. 10/956,454, filed on Oct. 1, 2004, now Pat. No. 7,775,999.

(51) Int. Cl.
A61F 5/37 (2006.01)
A61F 13/00 (2006.01)
A61F 5/00 (2006.01)
A61F 13/06 (2006.01)
A61B 19/00 (2006.01)
A61L 15/00 (2006.01)

(52) U.S. Cl. ........... 602/24; 602/23; 602/25; 602/60; 602/61; 602/62; 602/75; 128/846; 128/869; 128/870; 128/876; 128/882

(58) Field of Classification Search .......... 602/4, 19, 602/23–25, 60–62, 75; 128/845, 869, 882; 473/215, 277

See application file for complete search history.

(56) References Cited

U.S. PATENT DOCUMENTS

| 976,564 | A | 11/1910 | Riebel |
| 4,524,760 | A | 6/1985 | Lerner |
| 4,593,697 | A | 6/1986 | Salort |
| 4,709,692 | A | 12/1987 | Kirschenberg et al. |
| 4,901,710 | A | 2/1990 | Meyer |
| 4,977,893 | A | 12/1990 | Hunt |
| 5,286,251 | A | 2/1994 | Thompson et al. |
| 5,423,852 | A | 6/1995 | Daneshvar |
| 5,425,702 | A | 6/1995 | Carn et al. |
| 5,445,114 | A | 8/1995 | Walker |
| 5,486,194 | A | 1/1996 | Kawasaki et al. |
| 5,814,001 | A | 9/1998 | Schwenn et al. |
| 5,928,175 | A | 7/1999 | Tanaka |
| 6,210,353 | B1 | 4/2001 | Barnes |
| 6,428,495 | B1 | 8/2002 | Lynott |
| 6,652,596 | B2 | 11/2003 | Smith et al. |
| 6,832,960 | B2 | 12/2004 | Thöny |
| 7,758,481 | B2 * | 7/2010 | Drennan ............... 482/124 |
| 7,814,576 | B2 * | 10/2010 | Nakazawa ............ 2/227 |
| 2002/0082537 | A1 | 6/2002 | MacAllister |
| 2003/0009120 | A1 | 1/2003 | MacAllister |
| 2004/0116260 | A1 * | 6/2004 | Drennan ............... 482/124 |
| 2004/0230150 | A1 | 11/2004 | West |
| 2006/0074365 | A1 | 4/2006 | Brown |

FOREIGN PATENT DOCUMENTS

DE 3122462 A 12/1982

* cited by examiner

Primary Examiner — Patricia Bianco
Assistant Examiner — Brandon Jackson
(74) Attorney, Agent, or Firm — John P. O'Banion

(57) ABSTRACT

A support apparatus comprising a waist band, a thigh band, a lateral vertical strap attached to said waist band and two extensions attached to said thigh band, and a medial vertical strap attached to said waist band then wrapping medially down around the thigh and attaching to the thigh band.

15 Claims, 6 Drawing Sheets

HIP BRACE APPARATUS AND METHOD OF USE

CROSS-REFERENCE TO RELATED APPLICATIONS

This application is a continuation of U.S. patent application Ser. No. 10/956,454 filed Oct. 1, 2004, now U.S. Pat. No. 7,775,999, incorporated herein by reference in its entirety.

This application is related to U.S. Patent Application Publication No. U.S. 2006/0074365 A1, published on Apr. 6, 2006, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND

1. Field of the Disclosure

The present invention relates to apparatus for supporting a person's hip.

2. The Prior Art

The present invention is designed to enhance biomechanical function. In particular the present invention is designed to alleviate pain associated with arthritis, labrum tears, loose bodies, post surgical hip replacement or arthroscopy, prophylactic support to help minimize worsening of pathologic conditions, following surgery, or to help prevent surgery. Also, it is designed to enhance biomechanical function and duration of strenuous activities such as athletics or physical labor. It also enhances mechanical stability of the lower lumbar spine and pelvis.

Other braces are rigid, using plastic and/or metal components and predominately are designed for limiting hip joint motion. The present embodiment brace is elastic, light weight, and provides for enhanced biomechanical function.

BRIEF DESCRIPTION OF THE DRAWING FIGURES

DETAILED DESCRIPTION

Figure 1:
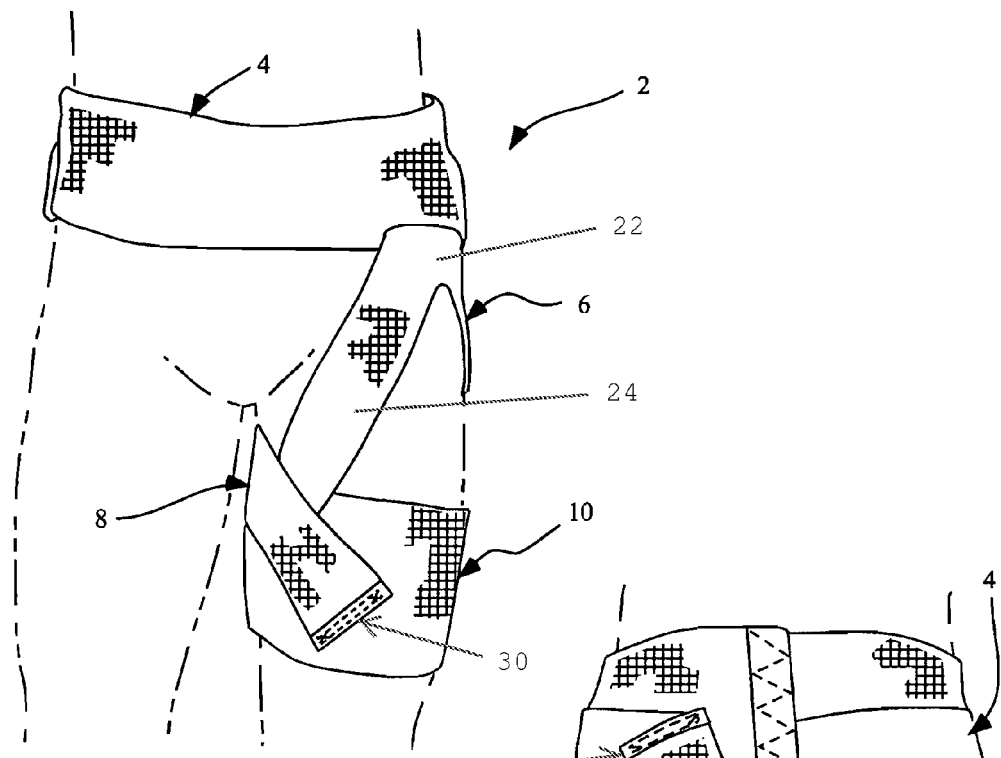
FIG. 1 is a front view of one embodiment of the hip brace as worn.

Persons of ordinary skill in the art will realize that the following description is illustrative only and not in any way limiting. Other modifications and improvements will readily suggest themselves to such skilled persons having the benefit of this disclosure. In the following description, like reference numerals refer to like elements throughout.

FIG. 1 is an anterior view of one embodiment of the hip brace 2 as worn. The hip brace 2 consists of a waist band 4, lateral vertical strap 6, medial vertical strap 8, and a thigh band 10. As seen in this view and also referring to FIG. 8, the base 22 of lateral vertical strap 6 is secured to the waist band 4 proximate to the side of the hip and a first extension 24 is secured proximate the anterior aspect of the thigh band 10 between the lateral and medial aspect of the thigh band 10. The medial vertical strap 8 is secured to the posterior of the waist band 4 (not seen) then wraps down and around the leg and is secured to the thigh band 10 proximate the anterior aspect of said thigh band 10 between the lateral and medial aspect. In another embodiment, elastic bands may be added to the interior of the waist band to increase the elasticity of the waist band.

Figure 2:
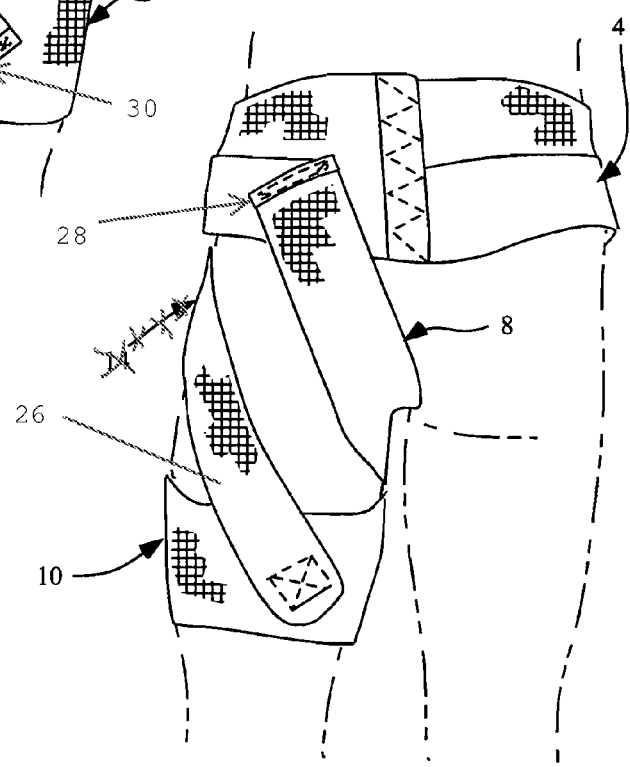
FIG. 2 is a posterior view of one embodiment of the hip brace as worn.

FIG. 2 is a posterior view of one embodiment of the hip brace 2 as worn. As seen in this view and also referring to FIG. 1 and FIG. 9, the first end 28 of medial vertical strap 8 is attached to the waist band 4 at the posterior of the hip. The medial vertical strap 8 wraps down and around the leg to the anterior aspect of said thigh band 10 between the lateral and medial aspect, and the second end 30 of medial vertical strap 8 is attached to the thigh band 10. The second extension 1-4 26 of the lateral vertical strap 6 wraps down and around the thigh and the end of the second extension is attached to the posterior of the thigh band 10.

Figure 3:
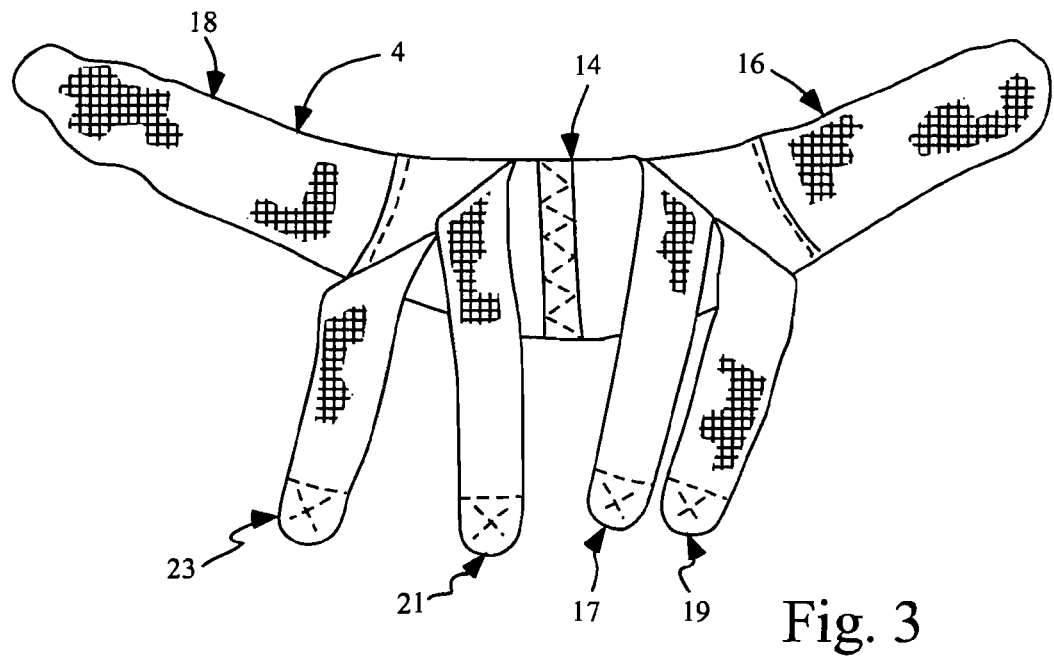
FIG. 3 is a view of the waist band 4.

FIG. 3 is a view of the waist band 4. The waist band 4 consists of a first layer 14, which includes a right flap 16 and a left flap 18. The right and left flap 16, 18 are attached to the first layer 14. The waist band 4 is manufactured from an elastic material such as neoprene. Further, the interior surface is smooth. The exterior surface of the right and left flap consists of a hook and loop system for attaching lateral vertical strap, medial vertical strap and a utility strap. The first layer 14 is wrapped tightly around the user's waist and may be secured at the right flap 16 and a left flap 18 by use of a hook and loop system, a buckle or a combination of the two. In the present embodiment, the right and left flap 16, 18 are sewn to the first layer 14 proximate a midpoint of the waist band 4. The right and left flap 16, 18 are used for securing the lateral vertical strap 6 and a utility strap 12. The right flap 16 is secured to the left flap 18 by use of a hook and loop system, a buckle or a combination of the two. In another embodiment, the right and left flaps 16, 18 may be secured to the first layer and/or each other using a hook and loop system. In a further embodiment, the second layer may consist of right flaps 17, 19 and left flaps 21, 23 may consist of a plurality of flaps or single flaps to which are secured to each other as described above.

Figure 4:
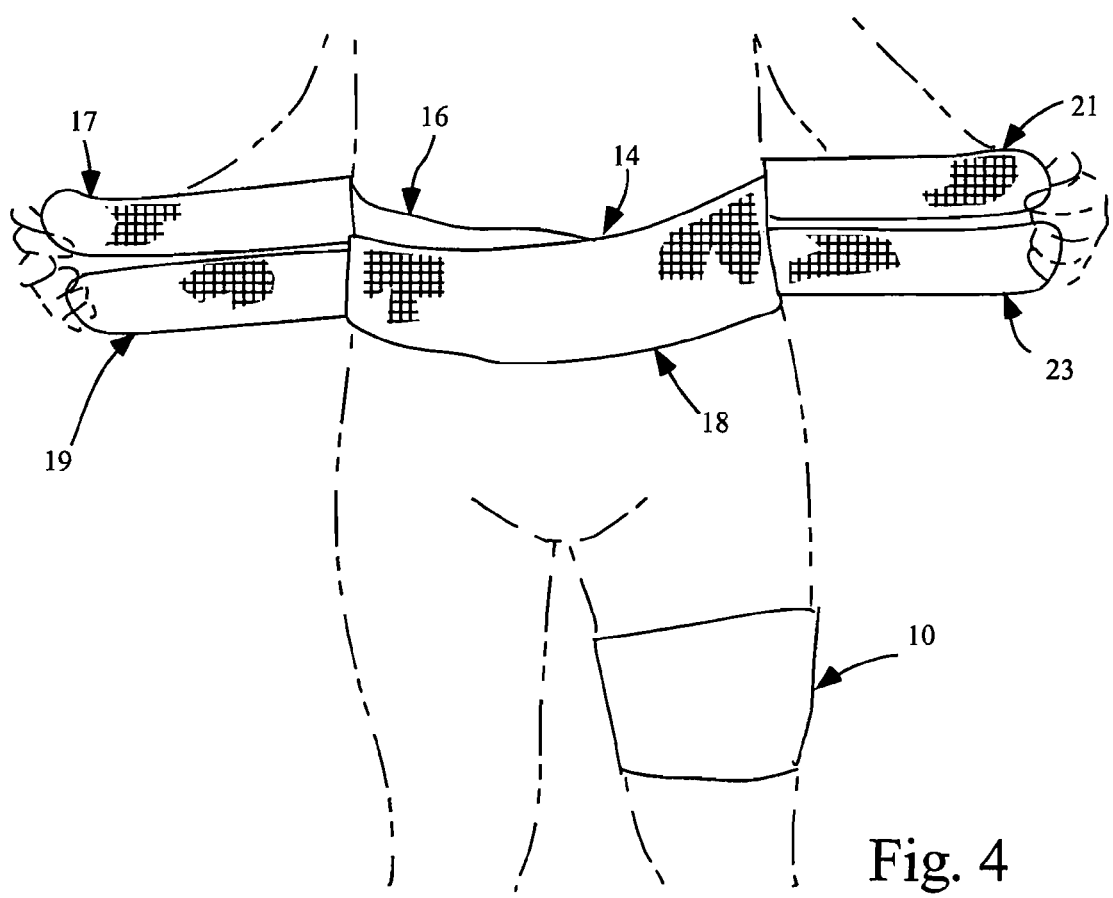
FIG. 4 is a person installing the waist band.

FIG. 4 is a person installing the waist band 4. In this instance, the person has wrapped the first layer of the waist band 4 around the waist. In the present embodiment, the waist band 4 is being held in place by a hook and loop system. The right and left flap 16, 18 are secured to the persons waist. The second layer may consist of either a single flap on either side or a dual flap system as shown. The right dual flaps 17, 19 and the left dual flaps 21, 23 are being held by the person.

Figure 5A:
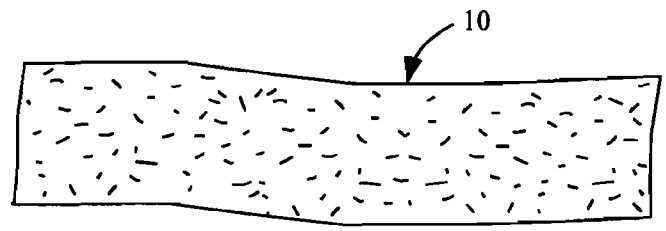
FIG. 5a is a drawing of one side of the thigh band.
Figure 5B:
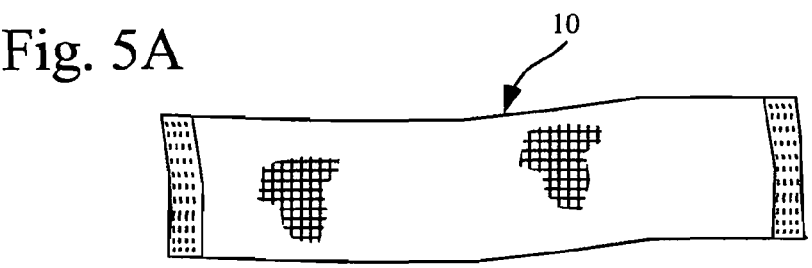
FIG. 5b is a drawing of the other side of the thigh band.

FIG. 5A is a drawing of one side of the thigh band 10. The thigh band 10 is wrapped around a person's thigh just above the knee and secured by a system of hooks and loops, a buckle or a combination of the two. In the present embodiment the thigh band 10 is manufactured from an elastic material such as neoprene. Further, the interior surface is smooth. The exterior surface consists of a hook and loop system for attaching lateral vertical strap, medial vertical strap and a utility strap. FIG. 5 5B is a drawing of the other side of the thigh band 10. In another embodiment, the thigh band 10 may be contoured for a better fit.

Figure 6:
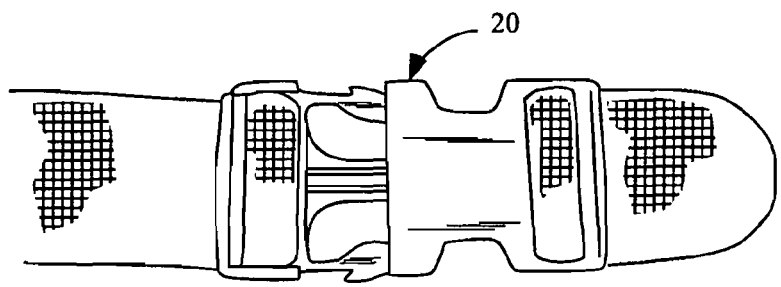
FIG. 6 is a drawing of a buckle for securing the waist band.

FIG. 6 is a buckle 20 for securing the single flap version of the waist band 4. The buckle 20 may be substituted for the right and left flaps of the second layer of the waist band 4.

Figure 7:
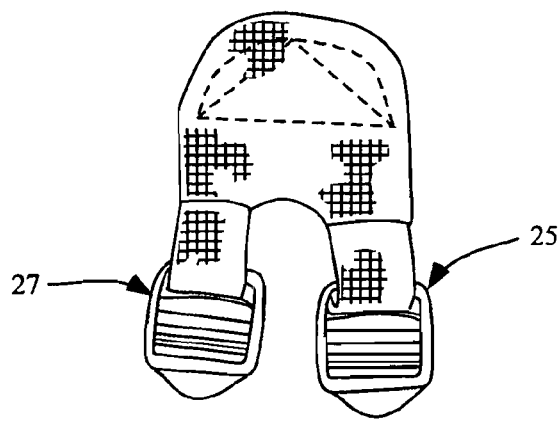
FIG. 7 is a drawing of another embodiment of the buckle for securing the waist band.

FIG. 7 is a dual buckle system 25, 27 for securing the second layer of the waist band which incorporates the right dual flaps 17, 19 and the left dual flaps 21, 23.

Figure 8:
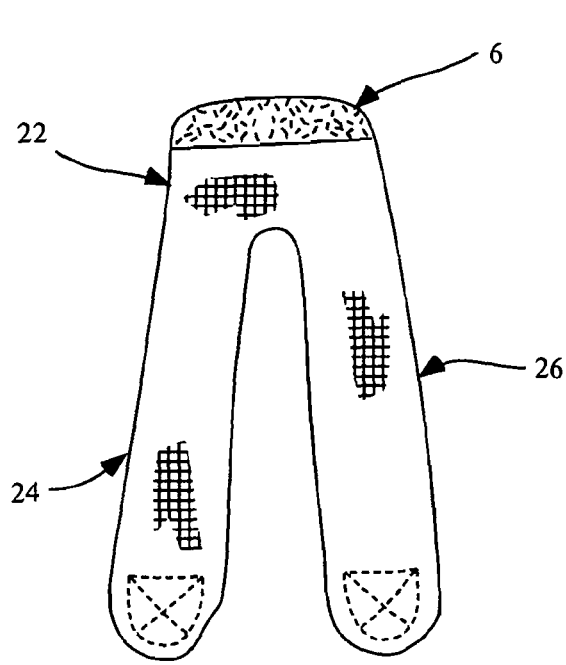
FIG. 8 is a drawing of the lateral vertical strap.

FIG. 8 is a drawing of the lateral vertical strap 6. The lateral vertical strap 6 is manufactured from an elastic material such as neoprene. In the present embodiment the lateral vertical strap 6 is manufactured from 4 mm neoprene. The lateral vertical strap 6 consists of a base 22, a first extension 24 and a second extension 26. The base 22 also consists of a hook and loop system that allows the base 22 to be secured to the waist band 4. A hook and loop system on the first and second extensions 24, 26 opposite the base 22 A allows the first and second extensions 24, 26 to be secured to the thigh band 10.

Figure 9:
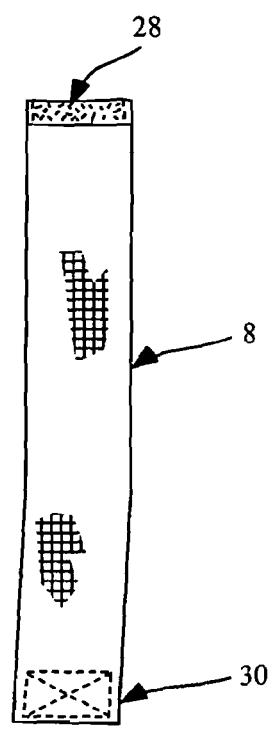
FIG. 9 is a drawing of the medial vertical strap.

FIG. 9 is a drawing of the medial vertical strap 8. The medial vertical strap 8 is manufactured from an elastic material. The medial vertical strap 8 consists of a first end 28 and a second end 30. Both the first end 28 and a second end 30 consists of a hook and loop system that allows the first end 28 to be secured to the waist band and the second end 30 to be secured to the thigh band.

Figure 1A:
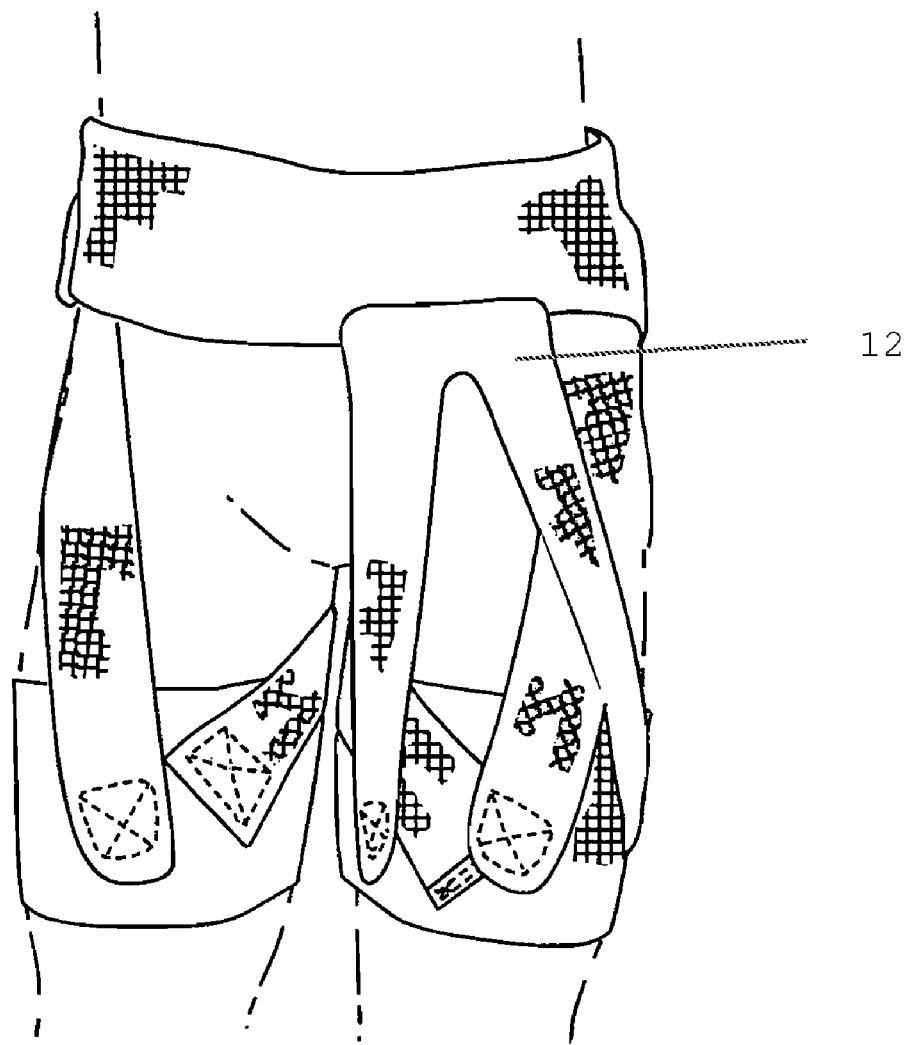
FIG. 1A is a front view of one embodiment of the hip brace as worn in a bilateral configuration with a utility strap.
Figure 10:
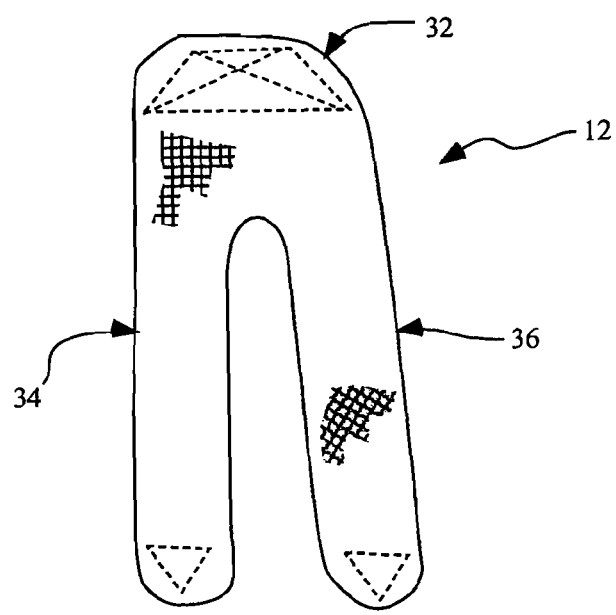
FIG. 10 is a drawing of the utility strap.

FIG. 10 is a drawing of the utility strap 12. The utility strap 12 is similar to the lateral vertical strap except smaller. In shorter people the utility strap 12 may be used as a replacement for the lateral vertical strap or, referring also to FIG. 1A, it may be used in conjunction with the lateral vertical strap for added support. The utility strap 12 is manufactured from an elastic material such as neoprene. In the present embodiment the utility strap 12 is manufactured from 3 mm neoprene. The utility strap 12 consists of a base 32, a first extension 34 and a second extension 36. The base 32 also consists of a hook and loop system that allows the base 32 to be secured to the waist band. On the first and second extensions 34, 36 opposite the base 32 also consists of a hook and loop system that allows the first and second extensions 34, 36 to be secured to the thigh band.

Figure 11:
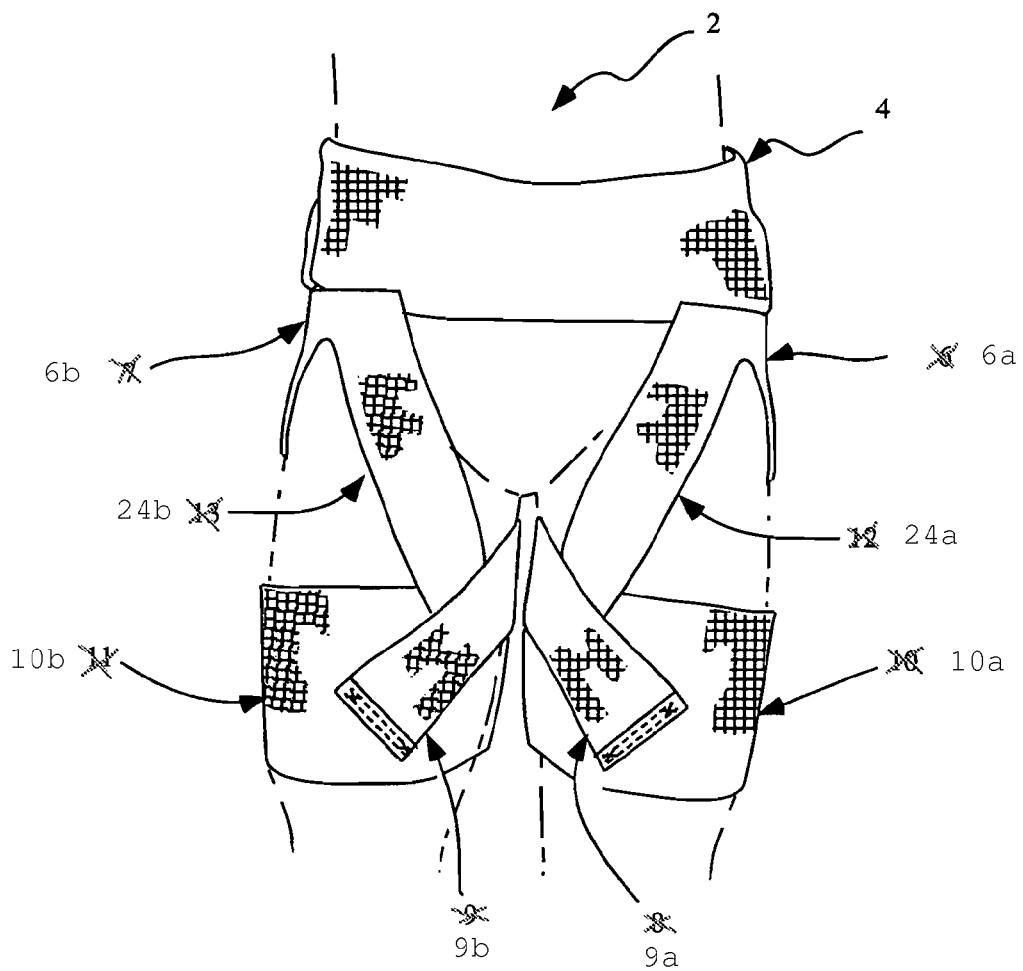
FIG. 11 is an anterior view of one embodiment of the hip brace as worn in a bilateral configuration.

FIG. 11 is an anterior view of one embodiment of the hip brace 2 as worn in a bilateral configuration. The hip brace 2 consists of a waist band 4, a first and second lateral vertical strap 6*a*, *b*, a first and second medial vertical strap 8*a*, 8*b*, and a first and second thigh band 10*a* 10*b*. As seen in this view both the first and second lateral vertical strap 6*a*, 6*b* are secured to the waist band 4 proximate to the side of the hip and a first extension 24*a*, 24*b* is secured proximate the anterior aspect of the thigh band 10 between the lateral and medial aspect of the thigh band 10. Both of the medial vertical straps 8*a*, 8*b* are secured to the posterior of the waist band 4 (not seen) and wrap down and around the leg and are secured to the thigh bands 10*a* 10*b* proximate the anterior aspect of said thigh band 10*a* 10*b* between the lateral and medial aspect of the thigh bands 10*a* 10*b*.

While embodiments and applications of this disclosure have been shown and described, it would be apparent to those skilled in the art that many more modifications and improvements than mentioned above are possible without departing from the inventive concepts herein. The disclosure, therefore, is not to be restricted except in the spirit of the appended claims.

What is claimed is:

1. A support apparatus comprising:
    a waist band adapted to be wrapped around a person's waist;
    a thigh band adapted to be wrapped around one of the person's thighs proximate to the person's knee;
    a lateral vertical strap adapted to be secured to the waist band, said lateral vertical strap having a first extension and a second extension, said first extension adapted to be secured to the thigh band proximate the anterior aspect of the thigh band between the lateral and medial aspects of the thigh band, said second extension adapted to be secured to the posterior of the thigh band; and
    a medial vertical strap having a first end and a second end, said medial vertical strap adapted to be wrapped around the person's leg, said first end adapted to be secured to the posterior of the waist band and said second end adapted to be secured to the thigh band proximate the anterior aspect of said thigh band between the lateral and medial aspect of the thigh band.

2. The apparatus of claim 1, wherein said waist band further comprises:
    a first layer having an interior and exterior, said exterior having a hook and loop system; and
    a second layer having a right flap and a left flap, said right flap and left flap attached to the first layer at a point proximate to a midpoint of said first layer.

3. The apparatus of claim 2, wherein said waist band further comprises: a first end and a second end, said first end removeably fastened to said second end.

4. The apparatus of claim 3, further comprising:
    a hook and loop system to fasten said first end and said second end of said waist band and said right and left flap.

5. The apparatus of claim 4, further comprising:
    a buckle system to fasten said first end and said second end of said waist band and said right flap and said left flap.

6. The apparatus of claim 5, wherein said waist band is manufactured from neoprene.

7. The apparatus of claim 6, wherein said neoprene is 2-3 mm thick.

8. A method for supporting a person's hip comprising:
    providing a waist band adapted to be wrapped around a person's waist;
    wrapping the waist band around the person's waist;
    providing a thigh band adapted to be wrapped around one of said person's thighs proximate to said person's knee;
    wrapping the thigh band around one of the person's thighs proximate to the person's knee;
    providing a lateral vertical strap adapted to be secured to said waist band, said lateral vertical strap having a first extension and a second extension, said first extension adapted to be secured to the thigh band proximate the anterior aspect of the thigh band between the lateral and medial aspects of the thigh band, said second extension adapted to be secured to the posterior of the thigh band;
    securing the lateral vertical strap to the waist band;
    securing the first extension to the thigh band proximate the anterior aspect of the thigh band between the lateral and medial aspects of the thigh band;
    securing the second extension to the posterior of the thigh band;
    providing a medial vertical strap having a first end and a second end, said medial vertical strap adapted to be wrapped around the person's leg, said first end adapted to be secured to the posterior of the waist band and said second end adapted to be secured to the thigh band proximate the anterior aspect of said thigh band between the lateral and medial aspect of the thigh band;

wrapping the medial vertical strap around the person's leg;

securing the first end of the medial vertical strap to the posterior of the waist band; and securing the second end of the medial vertical strap to the thigh band proximate the anterior aspect of said thigh band between the lateral and medial aspect of the thigh band.

9. The method of claim 8, wherein said waist band further comprises:

a first layer having an interior and exterior, said exterior having a hook and loop system; and a second layer having a right flap and a left flap, said right flap and left flap attached to the first layer at a point proximate to a midpoint of said first layer.

10. The method of claim 9, wherein said waist band further comprises:

a first end and a second end, said first end removeably fastened to said second end.

11. The method of claim 10, wherein said waist band further comprises:

a hook and loop system to fasten said first end and said second end of said waist band and said right and left flap.

12. The method of claim 11, wherein said waist band further comprises:

a buckle system to fasten said first end and said second end of said waist band and said right flap and said left flap.

13. The method of claim 12, wherein said waist band is manufactured from neoprene.

14. The method of claim 13, wherein said neoprene is 2-3 mm thick.

15. A support apparatus comprising:

a waist band adapted to be wrapped around a person's waist;

a thigh band adapted to be wrapped around one of said person's thigh proximate to said person's knee; and a utility strap having a first end, a second end and a midpoint;

wherein said first end of said utility strap is removeably attached to said thigh band proximate the anterior aspect of the thigh band proximate the medial aspect of said thigh band;

wherein said midpoint of said utility strap is removeably attached to said waist band proximate the front of said person's hip; and wherein said second end of said utility strap is removeably attached to said thigh band proximate the anterior aspect of said thigh band proximate the lateral aspect of said thigh band.

* * * * *